US00PP13698P29

(12) United States Plant Patent
Hofmann

(10) Patent No.: US PP13,698 P2
(45) Date of Patent: Apr. 1, 2003

(54) NEW GUINEA IMPATIENS PLANT NAMED 'FISIMP 114'

(76) Inventor: Birgit Hofmann, Gassenweg 29, 56170 Bendorf (DE)

( * ) Notice: Subject to any disclaimer, the term of this patent is extended or adjusted under 35 U.S.C. 154(b) by 0 days.

(21) Appl. No.: 10/087,961

(22) Filed: Mar. 4, 2002

(51) Int. Cl.[7] ..... A01H 5/00
(52) U.S. Cl. ..... Plt./318
(58) Field of Search ..... Plt./318

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of New Guinea Impatiens plant named 'Fisimp 114', characterized by its upright, outwardly spreading, and uniformly mounded plant habit; freely branching and freely flowering habit; large rounded light purple-colored flowers with lighter purple-colored eye that are positioned above and beyond the foliage; and medium to dark green-colored leaves.

1 Drawing Sheet

BOTANICAL CLASSIFICATION/CULTIVAR DESIGNATION

*Impatiens hawkeri* cultivar Fisimp 114.

BACKGROUND OF THE INVENTION

The present Invention relates to a new and distinct cultivar of New Guinea Impatiens plant, botanically known as *Impatiens hawkeri*, and hereinafter referred to by the name 'Fisimp 114'.

The new Impatiens is a product of a planned breeding program conducted by the Inventor in Hillscheid, Germany. The objective of the breeding program is to develop new vigorous Impatiens cultivars that flower relatively early with large rounded flowers and attractive flower colors.

The new Impatiens originated from a cross made by the Inventor in July, 1999 of the *Impatiens hawkeri* cultivar Toga, disclosed in U.S. Plant Pat. No. 10,304, as the female, or seed, parent with the *Impatiens hawkeri* cultivar BFP-865, disclosed in U.S. Plant Pat. No. 11,445, as the male, or pollen, parent. The cultivar Fisimp 114 was discovered and selected by the Inventor as a flowering plant within the progeny of the stated cross in a controlled environment in Moncarapacho, Portugal in March, 2000.

Asexual reproduction of the new cultivar by terminal cuttings taken in Moncarapacho, Portugal, since March, 2000, has shown that the unique features of this new Impatiens are stable and reproduced true to type in successive generations.

SUMMARY OF THE INVENTION

The following traits have been repeatedly observed and are determined to be the unique characteristics of 'Fisimp 114'. These characteristics in combination distinguish 'Fisimp 114' as a new and distinct Impatiens cultivar:

1. Upright, outwardly spreading, and uniformly mounded plant habit.

2. Freely branching and freely flowering habit.

3. Large rounded light purple-colored flowers with a lighter purple-colored eye that are positioned above and beyond the foliage.

4. Medium to dark green-colored leaves.

Plants of the new Impatiens can be compared to plants of the female parent, the cultivar Toga. In side-by-side comparisons conducted by the Inventor in Hillscheid, Germany, plants of the new Impatiens differed from plants of the cultivar Toga in the following characteristics:

1. Plants of the new Impatiens were taller than plants of the cultivar Toga.

2. Flowers of plants of the new Impatiens were darker purple in color than flowers of plants of the cultivar Toga.

Plants of the new Impatiens can be compared to plants of the male parent, the cultivar BFP-865. In side-by-side comparisons conducted by the Inventor in Hillscheid, Germany, plants of the new Impatiens differed from plants of the cultivar BFP-865 in the following characteristics:

1. Plants of the new Impatiens were taller and more vigorous than plants of the cultivar BFP-865.

2. Plants of the new Impatiens had slightly lighter green-colored leaves than plants of the cultivar BFP-865.

3. Flowers of plants of the new Impatiens were slightly lighter purple in color than flowers of plants of the cultivar BFP-865.

Plants of the new Impatiens can also be compared to plants of the cultivar Balcelavgo, disclosed in U.S. Plant Pat. No. 11,652. In side-by-side comparisons conducted by the Inventor in Hillscheid, Germany, plants of the new Impatiens differed from plants of the cultivar Balcelavgo in the following characteristics:

1. Plants of the new Impatiens had light green-colored stems and peduncles whereas plants of the cultivar Balcelavgo had brownish red-colored stems and peduncles.

2. Plants of the new Impatiens had more narrow and slightly darker green-colored leaves than plants of the cultivar Balcelavgo.

3. Flowers of plants of the new Impatiens were slightly lighter purple in color than flowers of plants of the cultivar Balcelavgo.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a side perspective view of a typical flowering plant of 'Fisimp 114' grown in a container.

DETAILED BOTANICAL DESCRIPTION

The cultivar Fisimp 114 has not been observed under all possible environmental conditions. The phenotype may vary somewhat with variations in environment such as temperature and light intensity, without, however, any variance in genotype.

The aforementioned photograph, following observations and measurements describe plants grown in Langley, British Columbia, Canada, under commercial practice in a greenhouse. Rooted young plants were planted in 17.5-cm containers during the spring and the aforementioned photograph and following observations and measurements were taken during the summer about 17 weeks later. During the production of the plants, day temperatures ranged from 21 to 24° C. and night temperatures were about 17 to 18° C. In the following description, color references are made to The Royal Horticultural Society Colour Chart, 1995 Edition, except where general terms of ordinary dictionary significance are used.

Botanical classification: *Impatiens hawkeri* cultivar Fisimp 114.

Parentage:

*Female parent.*—*Impatiens hawkeri* cultivar Toga, disclosed in U.S. Plant Pat. No. 10,304.

*Male parent.*—*Impatiens hawkeri* cultivar BFP-865, disclosed in U.S. Plant Pat. No. 11,445.

Propagation:

*Type cutting.*—Terminal tip cuttings.

*Time to initiate roots.*—Summer: About 8 to 9 days at 24° C. Winter: About 10 days at 21° C.

*Time to produce a rooted cutting.*—Summer: About 15 days at 24° C. Winter: About 18 days at 21° C.

*Root description.*—Numerous, fibrous, and freely branching; 158D in color.

Plant description:

*General appearance.*—Upright, outwardly spreading, and uniformly mounded plant growth habit; freely branching habit, dense and bushy appearance; freely flowering. Moderately vigorous to vigorous.

*Crop time.*—From a rooted cutting, about 10 to 11 weeks are required to produce finished flowering plants in 12-cm containers.

*Plant height.*—About 22.6 cm.

*Plant diameter or spread.*—About 55 cm.

*Lateral branches.*—Quantity per plant: About 11. Length: About 18 cm. Diameter: About 1.1 cm. Internode length: About 5.25 cm. Texture: Smooth, glabrous. Color: 143C.

*Foliage description.*—Arrangement: Primarily in whorls. Length: About 13.3 cm. Width: About 4.6 cm. Shape: Narrowly elliptic. Apex: Acuminate. Base: Acute. Margin: Serrulate with ciliation. Texture: Smooth, slightly rugose; glabrous. Color: Young foliage, upper surface: 137A to 137B. Young foliage, lower surface: 139C. Fully expanded foliage, upper surface: 137A to 139A. Fully expanded foliage, lower surface: 138B. Venation, upper surface: 145A. Venation, lower surface: 145C. Petiole: Length: About 3.1 cm. Diameter: About 4.5 mm. Texture: Smooth, glabrous. Color, upper and lower surfaces: 145B to 145C.

Flower description:

*Flower type and flowering habit.*—Single; large rounded light purple-colored flowers; slightly cupped. Freely and continuously flowering; usually about 6 to 9 flowers and flower buds per lateral branch. Flowers positioned above and beyond the foliage and typically face parallel to the leaf canopy. Petals not persistent; gynoecium persistent. Flowers not fragrant.

*Flower longevity.*—Flowers last about 8 to 9 days on the plant.

*Flowering season.*—Year-round under greenhouse conditions. Plants begin flowering about 9 to 10 weeks after planting.

*Flower buds.*—Length: About 2.5 cm. Diameter: About 1.7 cm. Shape: Ovoid. Color: 75A.

*Flower length.*—About 7.1 cm.

*Flower width.*—About 6.7 cm.

*Flower depth.*—About 1.75 cm.

*Petals.*—Quantity: Five per flower, imbricate. Length: Banner petals: About 3.2 cm. Lateral and base petals: About 3.7 cm. Width: Banner petal: About 4.7 cm. Lateral and base petals: About 4.6 cm. Shape: Roughly cordate. Apex: Emarginate. Base: Attenuate. Margin: Entire. Aspect: Flat to slightly cupped. Texture: Smooth; satiny. Color: When opening, upper surface: 78B. When opening, lower surface: 78B to 78C. Fully opened, upper surface: 78B; towards the base or eye, close to 75D; color fading to 75A to 75B with subsequent development. Fully opened, lower surface: 78C to 78D.

*Spur.*—Quantity: One per flower. Length: About 5.9 cm. Diameter: At apex: About 0.5 mm. At flower: About 3 mm. Aspect: Curved. Color: Closest to 47D.

*Peduncles.*—Length: About 5.9 cm. Diameter: About 2 mm. Texture: Smooth, glabrous. Strength: Strong, flexible. Angle: About 45° from the lateral branch. Color: 144C; occasionally with longitudinal stripes, 48D.

*Reproductive organs.*—Androecium: Stamen number: Five fused at anthers, hooded; filaments free. Anther length: About 5.5 mm. Anther shape: Obovate. Anther color: 55A. Pollen amount: Moderate. Pollen color: 8D. Gynoecium: Pistil quantity: One per flower. Pistil length: About 5 mm. Stigma color: 18D. Style color: 18D. Ovary: Five-celled. Ovary color: Initially 143C, becoming 143A with development.

*Seed/fruit.*—Seed and fruit development has not been observed.

Disease/pest resistance: Plants of the new Impatiens have not been observed to be resistant to pathogens and pests common to Impatiens.

It is claimed:

1. A new and distinct cultivar of New Guinea Impatiens plant named 'Fisimp 114', as illustrated and described.

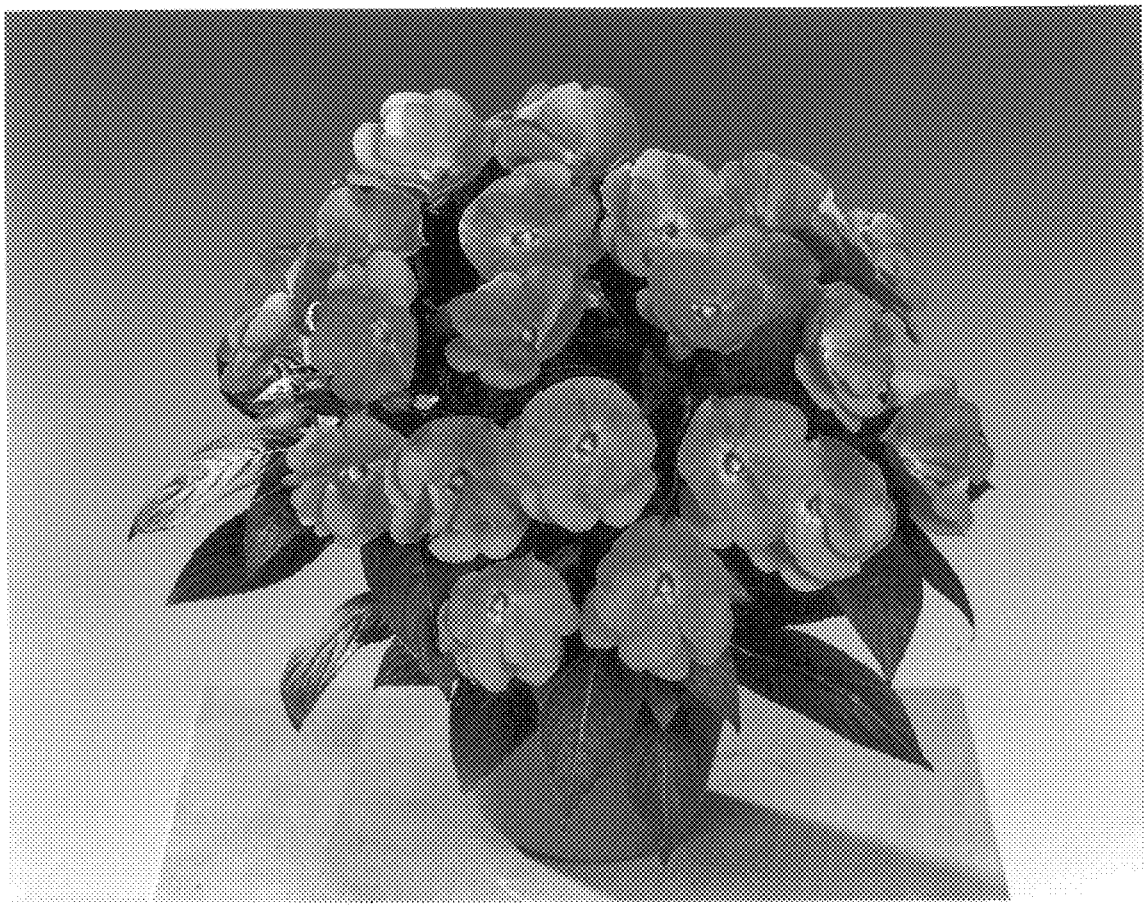

* * * * *